US006931888B2

(12) United States Patent
Shekunov et al.

(10) Patent No.: US 6,931,888 B2
(45) Date of Patent: Aug. 23, 2005

(54) LYOPHILIZATION METHOD AND APPARATUS FOR PRODUCING PARTICLES

(75) Inventors: Boris Y. Shekunov, Aurora, OH (US); Pratibhash Chattopadhyay, North Royalton, OH (US); Jeffrey S. Seitzinger, Broadview Heights, OH (US)

(73) Assignee: Ferro Corporation, Cleveland, OH (US)

( * ) Notice: Subject to any disclaimer, the term of this patent is extended or adjusted under 35 U.S.C. 154(b) by 37 days.

(21) Appl. No.: 10/434,435

(22) Filed: May 8, 2003

(65) Prior Publication Data

US 2004/0154317 A1 Aug. 12, 2004

Related U.S. Application Data

(60) Provisional application No. 60/445,941, filed on Feb. 7, 2003.

(51) Int. Cl.⁷ .......................... B01D 9/04; B01D 43/00; B01D 37/00; C02F 1/22; F26B 5/06
(52) U.S. Cl. ............................ 62/540; 62/541; 34/288; 210/808; 210/768
(58) Field of Search .................. 62/52.1, 532, 533, 62/534, 540, 541, 64; 34/288, 285; 210/808, 768, 774

(56) References Cited

U.S. PATENT DOCUMENTS 3,673,698 A * 7/1972 Guerard ...................... 34/284
5,084,187 A * 1/1992 Wilensky .................... 210/768

(Continued)

FOREIGN PATENT DOCUMENTS

JP 01-158042 6/1989

OTHER PUBLICATIONS

Sjostrom, Brita and Bergenstahl, Bjorn. Preparation of submicron drug particles in lecithin–stabilized o/w emulsions; I. Model studies of the precipitation of cholesteryl acetate, International Journal of Pharmaceutics 88 53–62 (1992) Elsevier Science Publishers B.V.

(Continued)

Primary Examiner—William C. Doerrier
(74) Attorney, Agent, or Firm—Rankin, Hill, Porter & Clark LLP

(57) ABSTRACT

A method and apparatus for producing particles, the apparatus includes a solution source that supplies a solution, and a fluid source that supplies a fluid. The solution includes a solvent and a solute. A mixer receives the solution and the fluid from the sources, and mixes the solution and the fluid together to form a mixture. The mixture is supplied from the mixer to an expansion assembly at first pressure. The expansion assembly sprays and expands the mixture substantially simultaneously to form frozen droplets, and preferably to form a low-density powder of frozen droplets. A freeze-dry apparatus sublimes the solvent from the particles. A high mass-transfer rate and a uniform open-structure of the powder bed enhances the freeze-drying process. Solid particles having a controlled size distribution are obtained. The particles preferably have a hollow or porous morphology suitable for differing drug delivery applications to include aerosol formulations.

14 Claims, 12 Drawing Sheets

U.S. PATENT DOCUMENTS

| | | | |
|---|---|---|---|
| 5,167,838 A | * 12/1992 | Wilensky | 210/768 |
| 5,290,827 A | 3/1994 | Shine | |
| 5,412,027 A | 5/1995 | Shine et al. | |
| 5,494,683 A | 2/1996 | Liversidge et al. | |
| 5,554,382 A | 9/1996 | Castor | |
| 5,567,769 A | 10/1996 | Shine et al. | |
| 5,639,441 A | 6/1997 | Sievers et al. | |
| 5,727,333 A | 3/1998 | Folan | |
| 5,750,679 A | 5/1998 | Haas et al. | |
| 5,766,637 A | 6/1998 | Shine et al. | |
| 5,776,486 A | * 7/1998 | Castor et al. | 424/450 |
| 5,921,478 A | 7/1999 | Kamiwano et al. | |
| 5,981,474 A | 11/1999 | Manning et al. | |
| 6,063,138 A | * 5/2000 | Hanna et al. | 23/295 R |
| 6,095,134 A | 8/2000 | Sievers et al. | |
| 6,214,384 B1 | 4/2001 | Pallado et al. | |
| 6,228,399 B1 | 5/2001 | Parikh et al. | |
| 6,248,363 B1 | 6/2001 | Patel et al. | |
| 6,284,282 B1 | * 9/2001 | Maa et al. | 424/499 |
| 6,299,906 B1 | 10/2001 | Bausch et al. | |
| 6,372,260 B1 | 4/2002 | Andersson et al. | |
| 6,384,090 B2 | 5/2002 | Riede et al. | |
| 6,387,409 B1 | 5/2002 | Khan et al. | |
| 6,391,452 B1 | 5/2002 | Antonsen et al. | |
| 6,414,050 B1 | 7/2002 | Howdle et al. | |
| 6,416,742 B1 | 7/2002 | Stefely et al. | |
| 6,440,337 B1 | 8/2002 | Hanna et al. | |
| 6,670,402 B1 | * 12/2003 | Lee et al. | 516/111 |
| 2002/0010982 A1 | * 1/2002 | Hanna et al. | 23/300 |
| 2002/0094318 A1 | 7/2002 | Lee et al. | |
| 2003/0026844 A1 | * 2/2003 | Lee et al. | 424/493 |
| 2003/0041602 A1 | 3/2003 | Williams, III et al. | |
| 2003/0215515 A1 | * 11/2003 | Truong-Le et al. | 424/489 |

OTHER PUBLICATIONS

Sjostrom, Brita and Bergenstahl, Bjorn. Preparation of submicron drug particles in lecithin–stabilized o/w emulsions; I. Model studies of the precipitation of cholesteryl acetate, International Journal of Pharmaceutics 84 107–116 (1992) Elsevier Science Publishers B.V.

Yoshinobu, Kawano; Shiomori, Koichiro; Kiyoyama, Shiro; Takeshita, Koichiro; and Hatate, Yasuo. Characteristics of Biodegradable Microcapsules by Solvent Evaporation in (W/O/W) Emulsion System Journal of Chemical Engineering of Japan vol. 34.

Nakajima, Akira; Hashimoto, Kazuhito; and Watanabe, Toshiya. Recent Studies on Super–Hydrophobic Films, Monatshefte fur Chemie 132, 31–41 (2001). Austria.

Chung, Tze–Wen; Huang, Yi–You; and Liu Yi–Ze. Effects of the rate of solvent evaporation on the characteristics of drug loaded PLLA and PDLLA microspheres, International Journal of Pharmaceutics 212 161–169 (2001).

* cited by examiner

LYOPHILIZATION METHOD AND APPARATUS FOR PRODUCING PARTICLES

1. REFERENCE TO RELATED APPLICATIONS

This application claims priority to provisional patent application Ser. No. 60/445,941, filed Feb. 7, 2003, the disclosure of which is hereby incorporated by reference in its entirety.

2. FIELD OF INVENTION

The present invention relates generally to an apparatus and a method of producing particles, and particularly to a method of using an apparatus to produce freeze-dried particles.

3. DESCRIPTION OF RELATED ART

Molecules of protein, peptide and other biological compounds require special consideration and handling during formulation and processing as a therapeutic or pharmaceutical. For example, contact with alcohols can denature some proteins and peptides. In addition, temperature extremes (hot or cold) can damage some proteins and peptides and reduce or eliminate biological activity.

Preparing protein therapeutics as dry powders is usually required to overcome stability problems with liquid formulations. A common process for making dry solid formulations of a biomaterial is freeze-drying, also known as lyophilization. This technique does not directly produce particles in the narrow micro- or nano-meter size range. Conventional lyophilization techniques are known to have uneconomically long process cycles (primary and secondary drying stages) and high energy cost. Further, inherent limitations of the conventional lyophilization include uneven moisture distribution, inconsistent stability, and unpredictable properties of the final product. Micro- or nano-meter size particles are preferred in various delivery systems and therefore further processing of the particles is required, for example, micronization is a process that reduces particle size. However, mechanical micronization can be time-consuming and inefficient for soft and ductile organic pharmaceuticals. Further, mechanical micronization can have an adverse effect on dry-powder formulation so as to render the formulation partially or completely ineffective.

The drying time for a typical freeze-drying or lyophilization is undesirable long because it is performed in several steps: primary drying to remove the loose solvent and secondary drying to remove solvent bonded to the solute. A cake with small, thin capillaries is usually produced during the primary drying process. The capillaries are the means by which the vapor travels to the surface and is removed. Thus, the smaller the capillary, the longer the time necessary for drying. Also, the capillaries are subject to collapse at elevated temperatures. So, the process is performed slowly at undesirably low temperatures (e.g. below −20 degrees Celsius). Therefore, current lyophilization techniques are uneconomical in terms of cost and time. Much of the cost can be ascribed to the length of the time required for the primary drying step, which can require several days to complete. It would be economically advantageous to increase sublimation rates and shorten primary drying times during lyophilization.

A spray-drying process or technique is used to produce pharmaceutically active particles. For example, the spray drying technique is useful to achieve the goal of producing dry powders of therapeutic proteins (such as insulin) for pulmonary delivery. An advantage of the spray-drying process is the direct production of particles that are porous or hollow. Spray drying reduces the need for micronization as a size-reducing processing step. In a particular spray-drying process, a sprayed drug solution or emulsion is used that includes an excipient. The excipient can serve as a blowing agent, and can stabilize the active compound during formulation. Spray-drying is particularly suitable for use with proteins and peptides that are labile or damaged by mechanical micronization. In addition, spray-drying is suitable for use with drugs having a narrow therapeutic index, and which require a very high fine particle fraction (FPF). A reduction of inter-particle interactions results in a corresponding increase of the FPF (in excess of 50%).

The excipient can produce porous or hollow structures in particles formed using the excipient. Porous particles are particularly suited for aerosol drug delivery because of their low particle density (about 0.1 g/cm$^3$). The low particle density results in a mass-median aerodynamic diameter (MMAD) that is smaller than the volume diameter by a factor of about three.

Unfortunately, conventional spray-drying is not a universal technique. The inlet temperature during operation is increased to remove a solvent; the temperature can exceed 100° C., and may be as high as 220° C. for aqueous solutions. The higher temperatures associated with conventional spray-drying can contribute to chemical and/or physical instability with reference to the active ingredient and/or the formulation excipient. Thus, thermally labile materials are precluded from use with the conventional spray-drying technique.

The disadvantageous elevated temperatures of spray-drying have been addressed in the art by various methods. One such method is spray freeze-drying, which involves the use of a solution containing a protein and an excipient. A solution is sprayed into a low-temperature liquid, for example, liquid nitrogen. The frozen droplets are then freeze-dried using a standard lyophilization procedure. Such processes are disclosed in U.S. Pat. No. 6,284,282, which is hereby incorporated by reference in its entirety.

Unfortunately, the low temperature of the low-temperature liquid, and the corresponding abrupt decrease of temperature during the spraying, can degrade some proteins, peptides and other biologically active materials. This can be especially problematic for a process that sprays small particles having a large specific surface area. A relatively long contact time of liquid droplets with dispersing gas can cause aggregation of protein molecules into a form that is inactive or has a reduced activity.

The drying of spray freeze-dried products is also performed in several steps similar to conventional lyophilization techniques described hereinabove. The drying time for spray freeze-drying is undesirable long and is performed at undesirably low temperatures. The abrupt temperature drop produces particles or a cake with small, thin capillaries. The capillaries are the means by which the liquid travels to the surface and is removed. Thus, the smaller the capillary, the longer the time necessary for drying. Also, the capillaries are subject to collapse at elevated temperatures. So, to ensure that the capillaries remain open, the process is performed at very low temperatures (below −40 Celsius). The droplet/air interface during the spraying stage may lead to protein de-activation or aggregation. Further, liquid nitrogen is difficult to handle on a large scale, and the process requires a liquid nitrogen receiving tank and/or multiple nozzles delivering freezing (liquid) nitrogen and dispersing (gaseous) nitrogen. The use of the liquid nitrogen is necessary in the conventional process to increase the consistency of freeze-drying process.

Vacuum-assisted freezing is another process for the preparation of small particles of temperature-sensitive compounds. In vacuum-assisted freezing, a solution is introduced into an evacuated chamber in the form of a spray. Droplets of the spray are at a sufficiently low temperature to freeze at the vacuum pressure inside the chamber. The frozen solvent is sublimated from the collected frozen droplets. Such a procedure is disclosed in U.S. Pat. No. 5,727,333, which is hereby incorporated by reference in its entirety. Unfortunately, the use of vacuum limits the solution throughput, and thus hinders industrial scale-up. A further disadvantage of the vacuum-assisted freezing technique is that the process temperature must be maintained in a very narrow temperature range for consistent freezing of droplets from cooled solutions. And, biologically active molecules can be damaged at the gas-liquid interface so that the biological activity is reduced.

Methods involving supercritical fluid (SCF) precipitation facilitate particle formation at near-ambient temperatures, and eliminate a need for a liquid-vapor interface. However, SCF precipitation has disadvantages because water and carbon dioxide ($CO_2$) are poorly miscible fluids, and therefore any precipitation technique using $CO_2$ and an aqueous solution requires the addition of an organic co-solvent to increase the solubility of water in $CO_2$. Unfortunately, the organic co-solvent is likely to be a protein denaturant. Many biologically active materials are irreversible degraded as a result of contacting the organic co-solvent. Loss of biological activity is also pronounced when the denaturing effect of organic solvent is exacerbated by an increased processing temperature.

Carbon dioxide-assisted nebulization with bubble-drying (CAN-BD) is a processing technique using a supercritical fluid. A CAN-BD process is disclosed in U.S. Pat. No. 5,639,441, which is hereby incorporated by reference in its entirety. The solubility of supercritical or compressed $CO_2$ in water or organic solvents is used in CAN-BD to generate small droplets or bubbles, and hot air or nitrogen is used to evaporate the solvent and form solid particles. The CAN-BD method is relatively simple, and allows for the processing of water-soluble compounds without use of organic solvents. CAN-BD claims the use of a reduced processing temperature relative to conventional spray-drying processing temperatures. Unfortunately, the CAN-BD processing temperature, of about 65° Celsius (C.) is still high enough to damage some proteins with or without co-formulation with an excipient. As in conventional spray-drying processes, there is a large droplet/vapor interface which may lead to protein aggregation or de-activation. In addition, it is problematic for the CAN-BD method to produce desirable porous or hollow particles. Generally, the production yield of small particles is low due to difficulties in collecting and retaining such small particles. The solvent content of particles produced is typically higher than the solvent content of particles produced by lyophilization. A high residual solvent content can create problems for long-term stability of some biological molecules. Further, CAN-BD has the disadvantage of an increased gas-liquid interfacial area, which potentially leads to aggregation and deactivation of proteins.

Aerogel processing has produced particles having a relatively high porosity and surface area. An example of aerogel processing is disclosed in the WIPO publication WO 02/051389, which is hereby incorporated by reference in its entirety. The aerogels are produced from modified organic carrier matrices. The matrices are saturated with a therapeutic agent, dried with supercritical $CO_2$ and micronized using a jet-mill. Measured aerogel densities are as low as 0.003 grams per cubic centimeter ($g/cm^3$).

The particles produced by aerogel processing have a relatively large volume diameter, and therefore may show reduced interparticle interactions and better aerosolization relative to high-density (>1 $g/cm^3$) solid particles. A disadvantage aerogel processing is the complexity and extensive use of organic solvents and reaction chemicals. The organic solvents and reaction chemicals can degrade a biologically active material or make the formulation otherwise unacceptable. Further, aerogel processing is not suitable for such common regulatory-accepted excipients as pure lactose, and may be problematic for industrial scale-up.

It would be desirable to have a particle formation method to produce particles of water-soluble compounds, such as thermo-labile therapeutic proteins or other biomaterials, with or without an excipient. It would further be desirable to have a particle formation method that produces uniform particles at desirable temperatures so as not to reduce the biologically activity of selected molecules. It also would be desirable to increase the consistency and to reduce the production cost of powders compared to standard lyophilization or spray-freeze drying techniques. And, it would be desirable to have a controllable method for producing particles suitable for aerosol formulations in a reduced time frame that is economical and desirable, and preferably at a relatively decreased capital cost for processing equipment.

SUMMARY OF THE INVENTION

The present invention provides a method and an apparatus to produce particles suitable for, for example, drug delivery systems, and porous particles for pulmonary and respiratory drug delivery using dry-powder inhalers (DPI) or metered dose inhalers (MDI).

The method of producing particles according to the invention includes a solution mixed together with a compressed fluid to form a mixture. The solution includes a solute dissolved in a solvent. The mixture is expanded into an expansion chamber to form droplets such that a portion of the fluid expands from a compressed state to a relatively uncompressed state. The expansion of the fluid portion reduces a temperature of the mixture to a temperature in a range that is below a freezing point of the solution. The solution droplets are frozen by the temperature reduction that occurs essentially simultaneously with the droplet atomization. The droplets are freeze-dried under vacuum to sublime the frozen solvent. The frozen solvent is thus removed from the particles, which comprise the solute and are substantially free of the solvent.

DESCRIPTION OF PREFERRED EMBODIMENTS

The present invention provides an apparatus and a method for producing particles. In a method according to the invention, a solution that includes a solvent and a solute is combined with a gas that is in a liquid, compressed or supercritical state (hereinafter collectively "fluid"). The combination of solution and fluid is expanded. The expansion of at least a portion of the fluid results in a temperature reduction of the solution and the fluid. As the temperature is reduced the solution freezes. The freezing solution preferably forms a multi-phase solid mixture consisting frozen solvent, frozen fluid and solute dispersed in the frozen solvent. The frozen solvent is sublimed in a freeze-drying process so that the solvent is removed and the solid solute particles are obtained.

Figure 1:
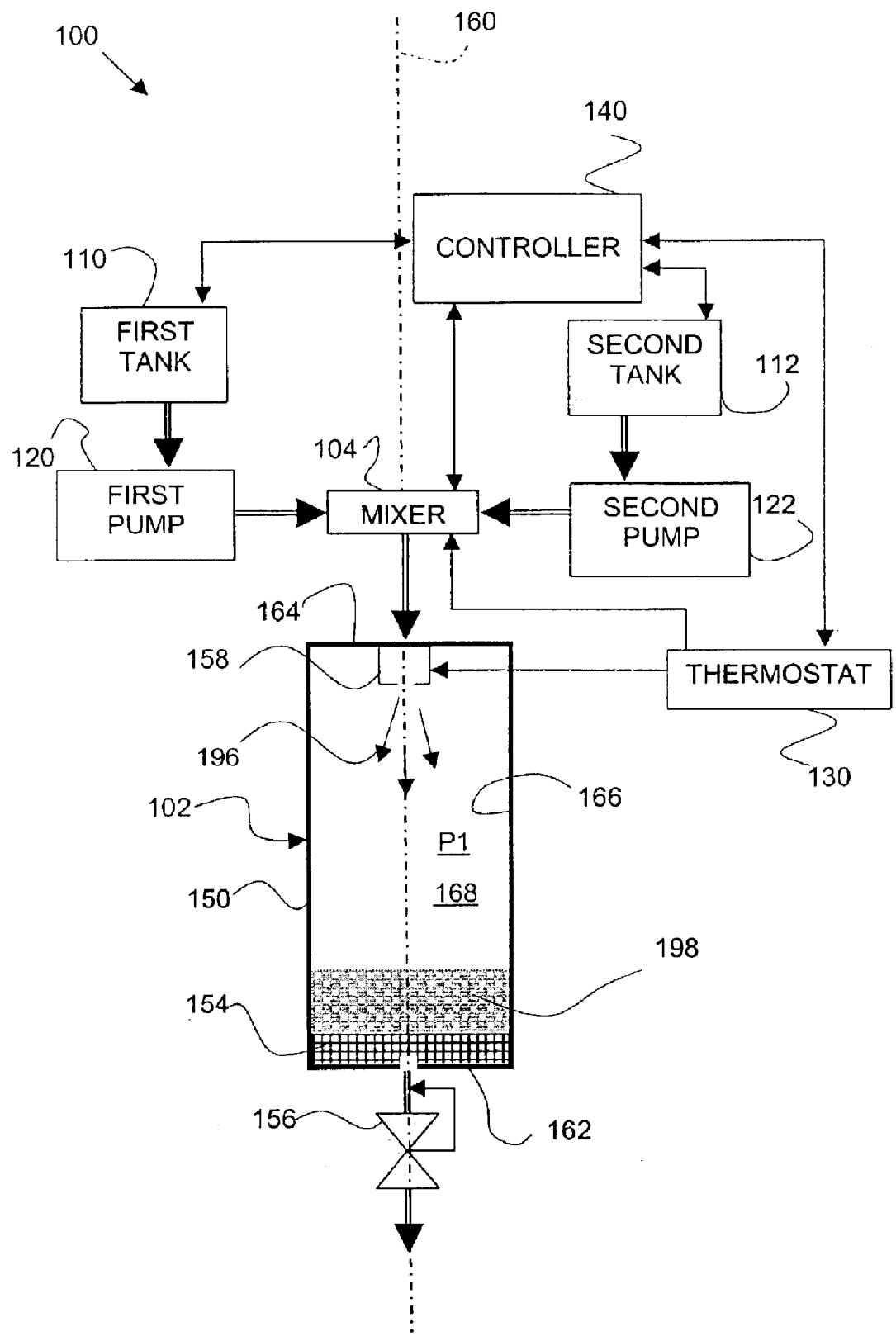
FIG. 1 is a schematic diagram of an apparatus for use with a method according to the invention.

A system or apparatus 100 for implementing a method according to the invention is shown in FIG. 1. The apparatus 100 includes an expansion assembly 102, a mixer 104, first and second supply tanks 110, 112, and first and second pumps 120, 122 that correspond to a respective one of the first and second supply tanks 110, 112. A thermostat 130 communicates with the expansion assembly 102, as described hereinbelow. A controller 140 communicates with various parts of the apparatus 100 so as to adjust and regulate the various parts.

The expansion assembly 102 includes an expansion vessel 150, a filter 154, a backpressure regulator 156, and a nozzle 158. The expansion vessel 150 is preferably cylindrical and defines an axis 160, and has a first end 162, and a second end 164 axially spaced from the first end 164. An inner surface 166 of the vessel 150 defines an expansion chamber 168. The pressure in the expansion chamber 168 is denoted with reference number P1. The filter 154 is disposed inside the chamber 168 adjacent to the first end 162 so that the filter 154 covers an outlet to the backpressure regulator 156.

The backpressure regulator 156 is preferably a model 26-1700 regulator, which is commercially available from Tescom, USA (Elk River, Minn.). The backpressure regulator 156 maintains the pressure P1 in the expansion chamber 168 in a predetermined range of pressures during operation of the apparatus 100.

The mixer 104 is in fluid communication with the expansion chamber 168 via the nozzle 158 that extends though a wall of the expansion vessel 150 into the expansion chamber 168 at the expansion vessel 150 first end 164. The mixer 104 is preferably a static mixer device. Suitable alternative mixers include both static and moving mixing devices, such as baffles, rotors, turbines, shear-mixers, ultrasonic dispersers, and other devices or mechanisms used to mix the solution and the fluid as supplied by the first and second pumps 120, 122, respectively.

The first or solution pump 120 is preferably a high-pressure liquid chromatography (HPLC) reciprocating pump, such as the model PU-2080, which is commercially available from Jasco Inc. (Easton, Md.). The solution pump 120 preferably has internal sensors that can electronically disable the solution pump 120 under predetermined conditions, for example at an unsafe internal pressure. Suitable alternative pumps include syringe type pumps, such as the 1000D or 260D pumps, which are commercially available from Isco Inc. (Lincoln, Nebr.).

The solution pump 120 is in fluid communication with the first tank 110, and with the mixer 104 so as to supply a solution from the first tank 110 to the mixer 104. The solution supplied from the first tank 110 includes a solvent and a solute. A most preferred solvent is water, but may be, or may include, tertiary butyl alcohol (TBA), ethanol, methanol, acetone, isopropyl alcohol, ethyl acetate or other organic or inorganic solvents, and combinations thereof.

The solute is preferably a biologically active material, for example, a drug, a pharmaceutical, or a therapeutic agent. Alternatively, the solute can be, for example, a medicinal agent, sugar, pigment, toxin, insecticide, viral material, diagnostic aid, agricultural chemical, nutritional material, protein, alkyloid, alkaloid, peptide, animal and/or plant extract, dye, explosive, paint, polymer precursor, cosmetic, antigen, enzyme, catalyst, nucleic acid, zeolite, polymer precursor, and combinations thereof. The solute can include an additional material, for example, a carrier, polymer, filler, disintegrant, binder, solubilizer, excipient, and combinations thereof. A preferred solute includes a biopharmaceutical material such as a protein, vaccine or anti-body and a sugar excipient or a polymer. The sugar excipient is, for example, sucrose, trehalose, mannitol, dextran, lactose, cyclodextrin, chitosan or other excipient(s) intended to stabilize the biopharmaceutical substance in the solid form. The polymer is, for example, a polysaccharide, polyester, polyether, polyanhydride, polyglycolide (PLGA), polylactic acid (PLA), polycaprolactone (PCL), polyethylene glycol (PEG), or polypeptide.

Surfactants, agents, buffers, emulsifiers, or modifiers and the like are added to the solution, as desired, to affect the relationship of the solute with the solvent in the solution. Preferred surfactants include non-ionic, anionic and cationic surfactants. Preferred emulsifiers include biodegradable surfactants such as TWEEN, SPAN, lethicin and also poly (vinyl pyrrolidone), polyglycerol, polyricinoleate, poly (vinyl alcohol), and block copolymers. TWEEN and SPAN are commercially available from ICI Americas, Inc. (Durham, N.C.).

Alternatively, the solution according to the present invention can be in the form of an emulsion, colloidal suspension, or a combination thereof. For example, an aqueous solution of a water-soluble drug can be combined with an aqueous suspension of a water-insoluble drug to form a solution according to the present invention.

The second or fluid pump 122 is preferably a P-200 high-pressure reciprocating pump commercially available from Thar Technologies, Inc. (Pittsburgh, Pa.). Suitable alternative pumps include diaphragm pumps and air-actuated pumps that provide a continuous flow of fluid. The fluid pump 122 preferably comes factory-equipped with a burst-type rupture disc, manufactured by Fike Inc. (Blue Springs, Mo.), which is plumbed into a pressure relief system.

The fluid pump 122 supplies fluid from the second tank 112 and through a surge tank (not shown) so as produce a pulse-free flow. The fluid pump 122 is in fluid communication the second tank 112 and the mixer 104 so as to supply the fluid from the second tank 112 to the mixer 104.

With reference to the fluid that the fluid pump 122 supplies to the mixer 104, as used herein and indicated hereinabove "fluid" includes supercritical fluid, and compressed gas and liquefied gas. The fluid is preferably supercritical carbon dioxide ("$CO_2$"). Suitable alternative fluids include nitrogen, nitrous oxide, ethane, propane, ammonia, hydrofluorocarbons (HFC or HFA), and other compressed or liquified gases exhibiting a sufficient expansion effect combined with their low temperature and/or Joule-Thompson effect to provide sufficient cooling during or after expansion.

The thermostat 130 communicates with heating elements (not shown) that are located proximate to the mixer 104 and the nozzle 158. A controller 140 communicates with and controls the mixer 104, the solution pump 120, the fluid pump 122, and the thermostat 130. Suitable controllers are commercially available, and are interchangeable therewith. In addition, the temperature of the expansion vessel 150 can be controlled using isolating materials or cooling jackets, which are also commercially available and interchangeable therewith.

Figure 2:
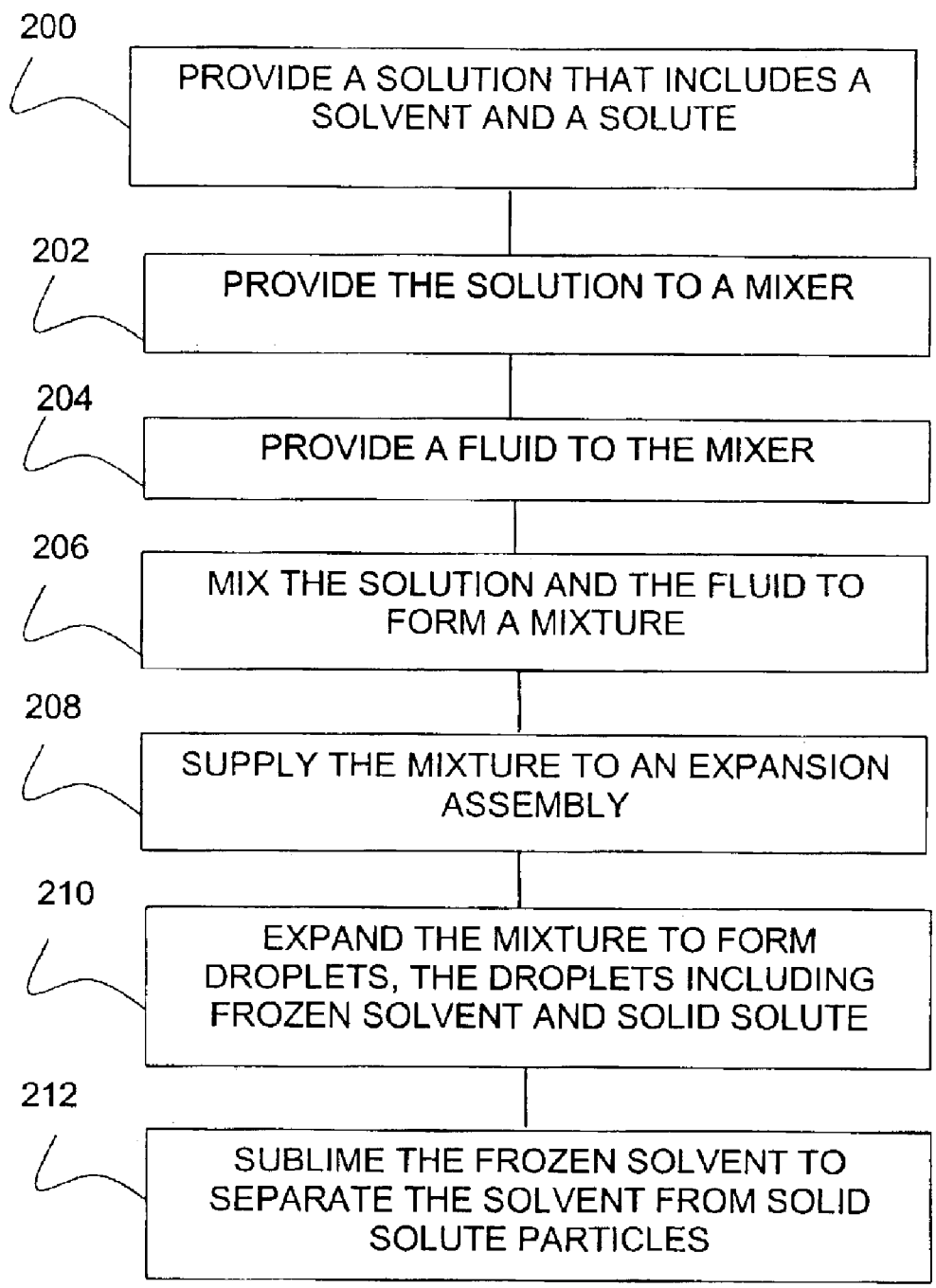
FIG. 2 is a block diagram of a method according to the invention.

During operation of the apparatus 100 and with reference to FIG. 2, the solution is prepared by dissolving a solute into a solvent (step 200). The controller 140 controls the thermostat 130 to adjust and regulate the temperature of the mixer 104 and the nozzle 158 to be at a temperature in a predetermined range of temperatures.

The controller 140 activates the solution pump 120 to supply a quantity of the solution to the mixer 104 (step 202). The controller 140 also activates the fluid pump 122 to supply a quantity of compressed fluid to the mixer 104 (step 204). The compressed fluid and the solution are contacted together in the mixer 104. The mixer 104 mixes the solution with the compressed fluid, and preferably the solution is saturated with the fluid (step 206) by the mixing.

The controller 140 controls the mixer 104 to supply the fluid-saturated solution to the expansion assembly 102 (step 208). In particular, the fluid-saturated solution is directed through the nozzle 158 into the expansion chamber 168. Because the pressure P1 in the expansion chamber 168 is reduced relative to the pressure of the fluid-saturated solution, the fluid-saturated solution expands upon exiting a nozzle orifice (step 210). The solution is atomized into droplets by the combined effect of the flow through the nozzle orifice, the partial dissolution of the fluid, and the subsequent fluid expansion. Arrows labeled with the reference number 196 denote the atomization.

Essentially simultaneously and in parallel with droplet formation, a portion of the compressed fluid in the fluid-saturated solution expands to a relatively uncompressed gaseous state, and as a result of the heat exchange between the solution and the fluid, preferably combined with well-known Joules-Thompson effect, the temperature of the solution droplets 196 decreases. As the temperature of the solution droplets 196 decreases, the solution droplets 196 freeze into solid particles 198 containing both solid solute and frozen solvent. Particle size, particle shape (morphology) and particle density (porosity) are controlled by adjusting operating parameters such as, for example, nozzle geometry, pressure, temperature, flow rate, composition and concentration of the solution, choice of fluid, the presence, type and/or amount of processing aid (e.g., surfactant), and combinations thereof.

A portion of the fluid may also freeze to form, for example, particles of dry ice (frozen carbon dioxide). The carbon dioxide formation is achieved when, naturally, carbon dioxide is the selected fluid, and the temperature in the expansion chamber 168 adjacent to the nozzle 158 is below about −56.5° C.

If dry ice formation is not desired, the controller 140 can control the thermostat 130 to regulate the temperature in the chamber 168 to be in a preferable range from about −80° C. to about 0° C. Alternatively the ratio between the solution and fluid can be increased to achieve a smaller Joule-Thompson effect or a smaller heat exchange effect. In addition, a temperature gradient can be created in expansion vessel 150 (temperature decreasing from the first end 162, to the second end 164) in order to produce particles free of solid fluid the first end 162.

Accordingly, particles of solute and solvent, and optionally particle of compressed fluid (eg. carbon dioxide crystals or dry ice), collect in the expansion chamber 168 adjacent to the first end 162. Gaseous fluid is removed from the chamber 168 through the backpressure regulator 156, and the filter 162 ensures that the particles 198 remain in the chamber 168.

The mixture of solid particles 198 is subjected to a freeze-drying process (step 212). That is, the frozen solvent is sublimated (phase change from solid to gas without an intervening liquid phase) from the mixture of solid particles 198 and particles of solvent and/or particles containing both solid solute and frozen solvent. Suitable freeze-drying techniques and the parts necessary to assemble a suitable and appropriate apparatus are commercially available.

Figure 3:
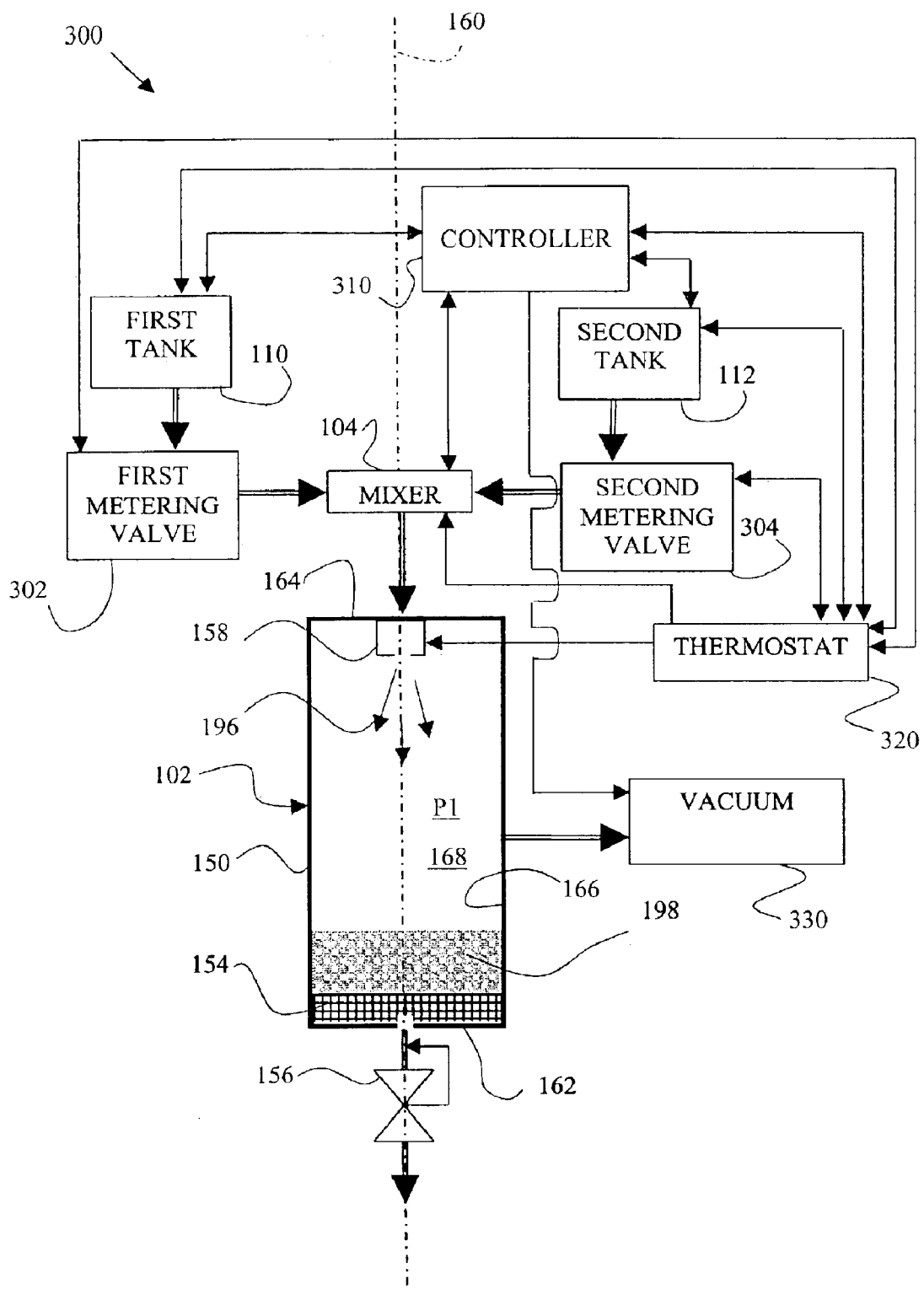
FIG. 3 is a schematic diagram of another apparatus for use with a method according to the invention.

As a result of the sublimation process, the particles 198 are substantially devoid of solvent and fluid and preferably have a highly porous structure. The mole fraction of solvent in the product is preferably smaller than 10% or more preferably smaller than 4%. The particles 198 have a size and morphology that is dependant on operating parameters discussed hereinabove. Typically, particles produced by a method according to the invention have a narrow particle distribution, and a diameter in the micron (micrometer) or sub-micron size range. The particles preferably form a homogeneous, easily-flowing powder. The powder preferably has a low bulk density (below 0.5 $g/cm^3$, more preferably below 0.1 $g/cm^3$) forming open structures with large and interconnected network of channels in the powder bed. If the pre-selected solute comprises a plurality of materials, the resultant composite particles can form, for example, microspheres or microcapsules. In addition, the particles can have a hollow or porous structure having a high surface area per volume and can be readily dispersible by an air flow. The particle porosity can be affected by selecting the process parameters to obtain frozen droplets 196. The enhanced particle porosity and reduced powder density are especially advantageous features of a lyophilization process according to the invention.

Because of the ability to create enhance porosity relative to conventional lyophilization techniques, the method according to the invention can be performed at desirable temperatures and/or at reduced times. Specifically, the method according to the invention can form particles in a loose, porous bed having many wide capillaries and a large surface area. The combination of wide capillaries and a large surface area results in a relatively fast mass-transfer and a reduced drying time. Further, the relatively fast mass-transfer increases the homogeneity of the particles formed. Thus, if desired, particles formed in accordance with the present invention have an increased porosity and a higher degree of uniformity than particles formed by conventional spray- or spray/freeze dry techniques.

An apparatus 300 in accordance with the present invention is shown in FIG. 3. The apparatus 300 includes many parts that are substantially the same as corresponding parts of the apparatus 100 shown in FIG. 1; this is indicated by the use of the same reference numbers for such corresponding parts in FIGS. 1 and 3. The apparatus 300 operates in a pulsed mode. Rather than having a plurality of pumps, the first and second tanks 110, 112 are in fluid communication with the mixer 104 though respective metering valves 302, 304. A controller 310 communicates with a thermostat 320 and a vacuum device 330 in addition to the controls discussed with reference to the previously described controller 140.

In a pulsed mode of operation, high throughput rates are achieved by discharging the contents of the first and second tanks 110, 112 through the respective metering valves 302, 302, and further through the mixer 104 into the expansion chamber 168. Because no pumps are plumbed in-line between the tanks 110, 112 and the mixer 104, the tanks 110, 112 are pressurized. The thermostat 320, under the control of the controller 310, regulates the temperatures of the tanks 110, 112, the metering valves 302, 304 and the nozzle 158.

During the pulsed mode of operation, the contents of one or more sets of tanks 110, 112 are flowed through the respective metering valves 302, 304, through the mixer 104 and into the chamber 168. The mixer 104 mixes the content of the tanks (the fluid and the solution) together to form a mixture. The mixture is provided to the expansion assembly 102, and specifically to the nozzle 158. The nozzle 158 sprays the mixture into the chamber 168, thus forming frozen/solid droplets, as described hereinabove, in a batch-wise manner. The frozen/solid droplets corresponding to the single or plural batches are freeze-dried using the vacuum 330. The gaseous solvent and fluid is removed from the solute particles. The pulse discharge mode of operation can decrease the risk of nozzle blockage by the formation of dry ice, and can increase the production rate.

Figure 4:
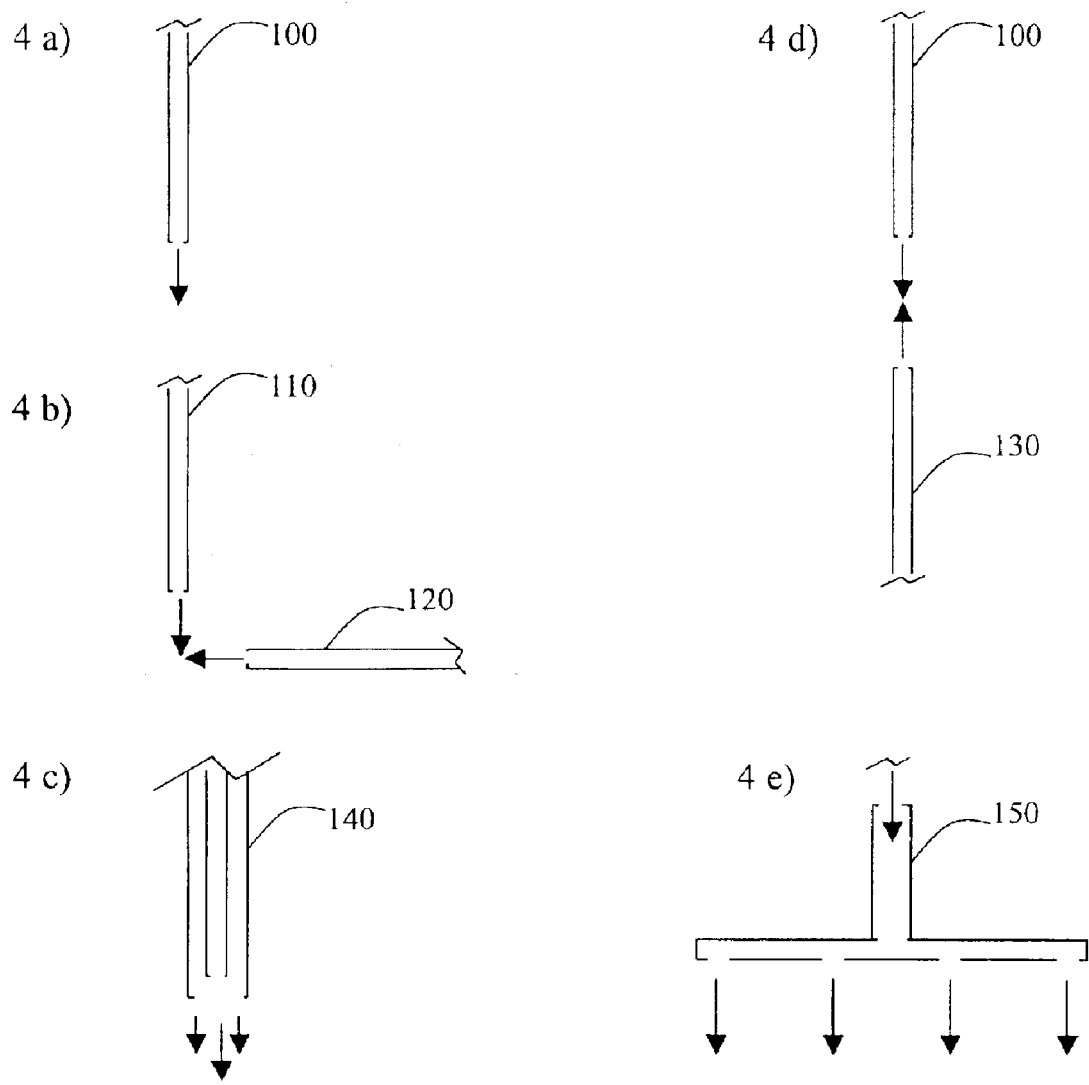
FIGS. 4(a)–4(e) are schematic diagrams of examples of nozzles suitable for use with a method according to the invention.

In an alternative method, a plurality of fluids is used, each fluid having a freezing point at a different temperature. In such a method, the fluid having the relatively lower freezing point acts as a blowing agent during the expansion step, and the fluid having the relatively higher freezing point crystallizes during the expansion step. Different configurations of nozzles using a plurality of fluids are shown in FIG. 4. A single capillary tube 100 carries a fluid with relatively high freezing point (such as $CO_2$) with pre-mixed solution (FIG. 4a) and corresponds to the main working regime shown in FIG. 1. Alternatively, a fluid with relatively low freezing point such as nitrogen is used as blowing gas for solution in capillary 110 and then mixed with expanding flow 120 of pure $CO_2$ (FIG. 4b). In another scheme (FIG. 4c) the blowing and freezing fluids are supplied co-axially (140) through the same nozzle. FIG. 4d represents a configuration in which $CO_2$ pre-mixed with solution expands towards the contra-flow of blowing gas 130 in order to control the temperature of the mixture or to enhance the droplet dispersion. Also two expanding flows of $CO_2$ pre-mixed with solution can be directed according to FIG. 4d to enhance the droplet dispersion. FIG. 4e represents a multiple orifice nozzle, which can be used for a large-scale production. According to this invention, the blowing and freezing fluids can be the same chemical entity (for example gaseous and liquid nitrogen, gaseous or liquid $CO_2$) or different chemical entities (for example gaseous nitrogen and liquid or supercritical $CO_2$).

EXAMPLES

The following examples are intended only to illustrate methods and embodiments in accordance with the invention, and as such should not be construed as imposing limitations upon the claims. Unless specified otherwise, all ingredients are commercially available from such common chemical suppliers as Sigma Aldrich, Inc. (St. Louis, Mo.) and/or Fisher Scientific International, Inc. (Hanover Park, Ill.).

Example 1

Preparation of Lactose Solution.

In an apparatus as shown in FIG. 3, 0.6 grams (g) of lactose was dissolved into 10 milliliters (ml) of purified water to form SOLUTION 1(a). SOLUTION 1(a) was charged to a solution tank and equilibrated for 20 minutes. The solution tank was pressurized with carbon dioxide gas to an operating pressure of 30 MegaPascal (MPa), and heated to a temperature of 20° Celsius (293 Kelvin (K)).

A FREEZONE, 4.5 Liter Model 77510 freeze-dry system, which is commercially available from Labconco Corporation (Kansas City, Mo.), was connected to an expansion assembly. Liquid carbon dioxide was charged to a fluid tank. The 10 ml of SOLUTION 1(a) from the solution tank was metered into a mixer, and about 10 ml of liquid carbon dioxide was also metered into the mixer. The mixer was operated at an agitation speed of about 4000 revolutions per minute (RPM). SOLUTION 1(a) and the liquid carbon dioxide were mixed in the mixer to form a liquid carbon dioxide/solution mixture.

Expansion and Freeze-drying of Lactose Particles.

The liquid carbon dioxide/solution mixture was directed from the mixer into the expansion assembly placed into stainless steel expansion vessel of about 2 L volume. In particular, the liquid carbon dioxide/solution mixture was sprayed through a nozzle into an expansion chamber. The nozzle was a multi-nozzle plate having 12 orifices of 180 micrometers ($\mu$m) diameter each similar to nozzle shown in FIG. 4e.

The pressure in the expansion chamber was at atmospheric pressure, and the pressure of the liquid carbon dioxide/solution mixture was maintained in the mixer at about 30 MPa. The expansion chamber temperature was maintained at below about 0° Celsius. The liquid carbon dioxide/solution mixture was sprayed through the nozzle Frozen solution particles and dry ice particles collected in the expansion chamber after spraying. The freeze-dry system was engaged and operated on the contents of the expansion chamber for about 12 hours.

Analysis of Lactose Particles.

Figure 5:
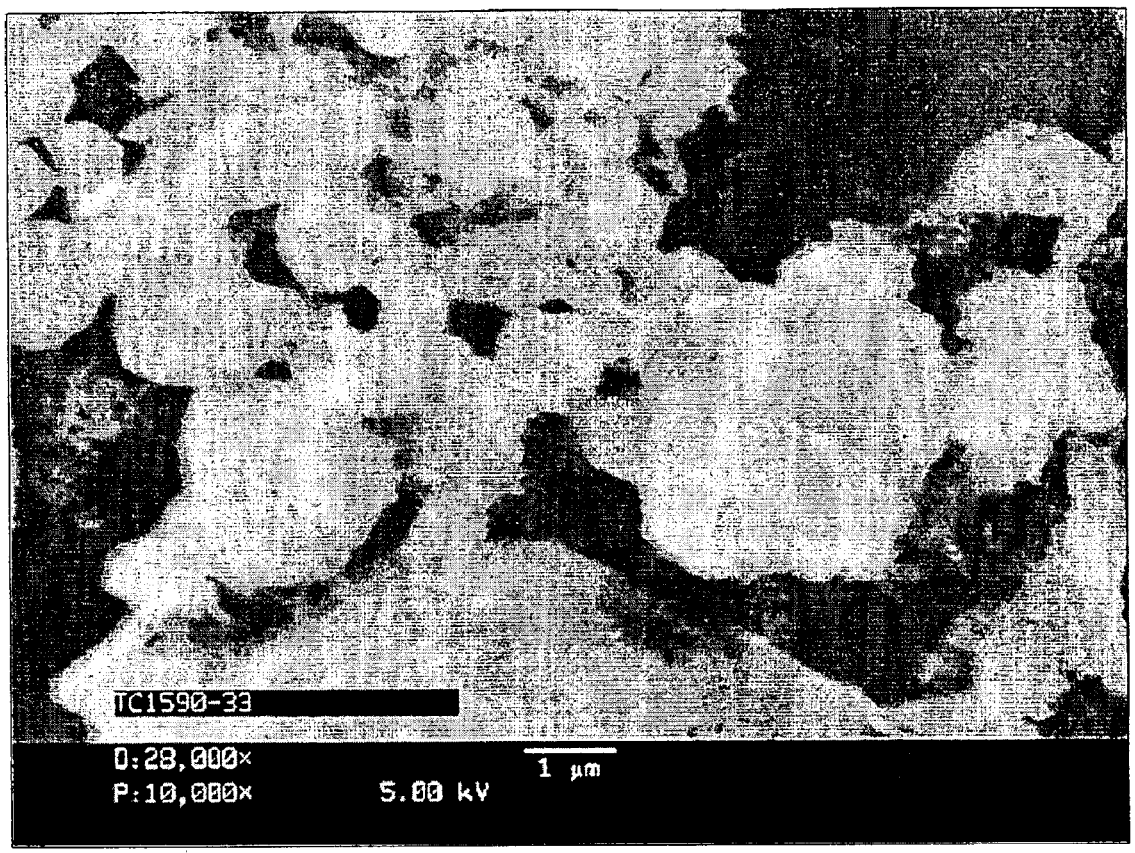
FIG. 5 is an SEM micrograph of Lactose particles produced in accordance with the invention in EXAMPLE 1.

Analysis of the lactose particles was performed using a Scanning Electron Microscope (SEM) to determine size and morphology. The dry product consisted of fine porous lactose particles having a diameter in a range of from 0.5 $\mu$m to 10 $\mu$m. FIG. 5 is an SEM micrograph of Lactose particles produced in EXAMPLE 1.

Example 2

Preparation of Lactose Solution.

The materials and processing conditions were the same as in EXAMPLE 1, except that the lactose solution was expanded with a larger volume of liquid carbon dioxide, about 50 ml.

Expansion and Freeze-drying of Lactose Particles.

The expansion and subsequent processing of the lactose particles was the same as in EXAMPLE 1.

Analysis of Lactose Particles.

Figure 6:
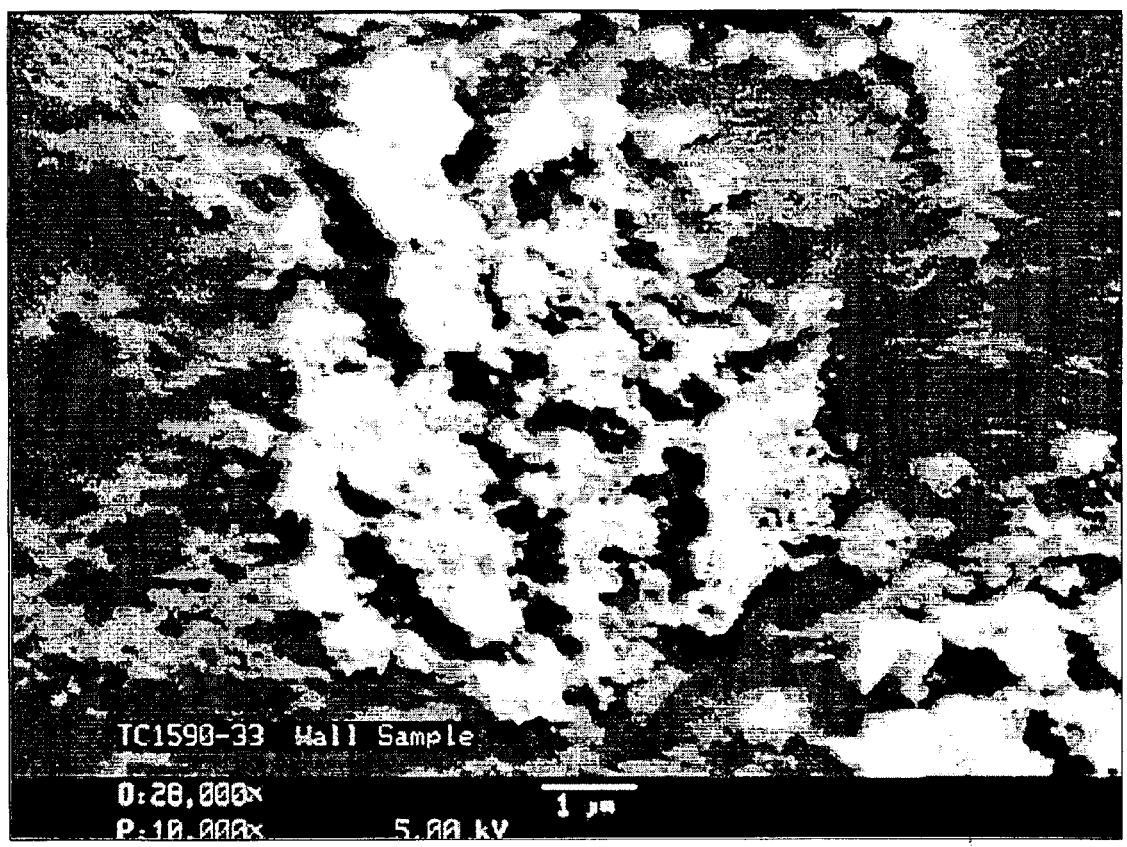
FIG. 6 is an SEM micrograph of Lactose particles produced in EXAMPLE 2.

Analysis of the lactose particles was performed using a Scanning Electron Microscope (SEM) to determine size and morphology. The dry product consisted of fine lactose particles having a mean particle diameter below 1 µm as shown in FIG. 6.

Example 3

Preparation of Lactose/Insulin Solution.

The materials and processing conditions were the same as in EXAMPLE 1, except that 1 gram of lactose and 0.2 grams of insulin were dissolved in 10 ml of purified water to form a lactose/insulin.

Expansion and Freeze-drying of Lactose/Insulin Particles.

The expansion and subsequent processing of the lactose/insulin particles was the same as in EXAMPLE 1.

Analysis of the Lactose/Insulin Particles.

Analysis of the lactose/insulin particles was performed using a Scanning Electron Microscope (SEM) to determine size and morphology. The dry product consisted of fine lactose and insulin particles having a mean particle diameter below 10 µm.

Example 4

Preparation of Lysozyme/Trehalose Solutions.

In an apparatus as shown in FIG. 1, two solutions of lysozyme and trehalose in purified water were prepared to form Lysozyme/Trehalose SOLUTIONS 4(a)–4(b). The compositions of SOLUTIONS 4(a)–4(b) are listed in TABLE 1.

Expansion and Freeze-drying of Lysozyme/Trehalose Particles.

SOLUTIONS 4(a)–4(b) were heated to a temperature, and sequentially metered into the system at flow rates, listed in TABLE 1, and allowed to equilibrate in a solution tank with $CO_2$ at 20 MPa. SOLUTIONS 4(a)–4(b) and the $CO_2$ were passed through a static mixing element before being expanded across the above-mentioned multi-orifice plate into the 2 L stainless steel expansion vessel.

The expansion chamber was at atmospheric pressure, and the temperature of this chamber was maintained at below about 0° C. Frozen particles of the Lysozyme/Trehalose solution and frozen particles of solvent were collected along with dry ice particles in the expansion chamber after spraying. The freeze-dry system was engaged and operated on the contents of the expansion chamber for about 12 hours.

Analysis of Lysozyme/Trehalose Particles

Figure 7:
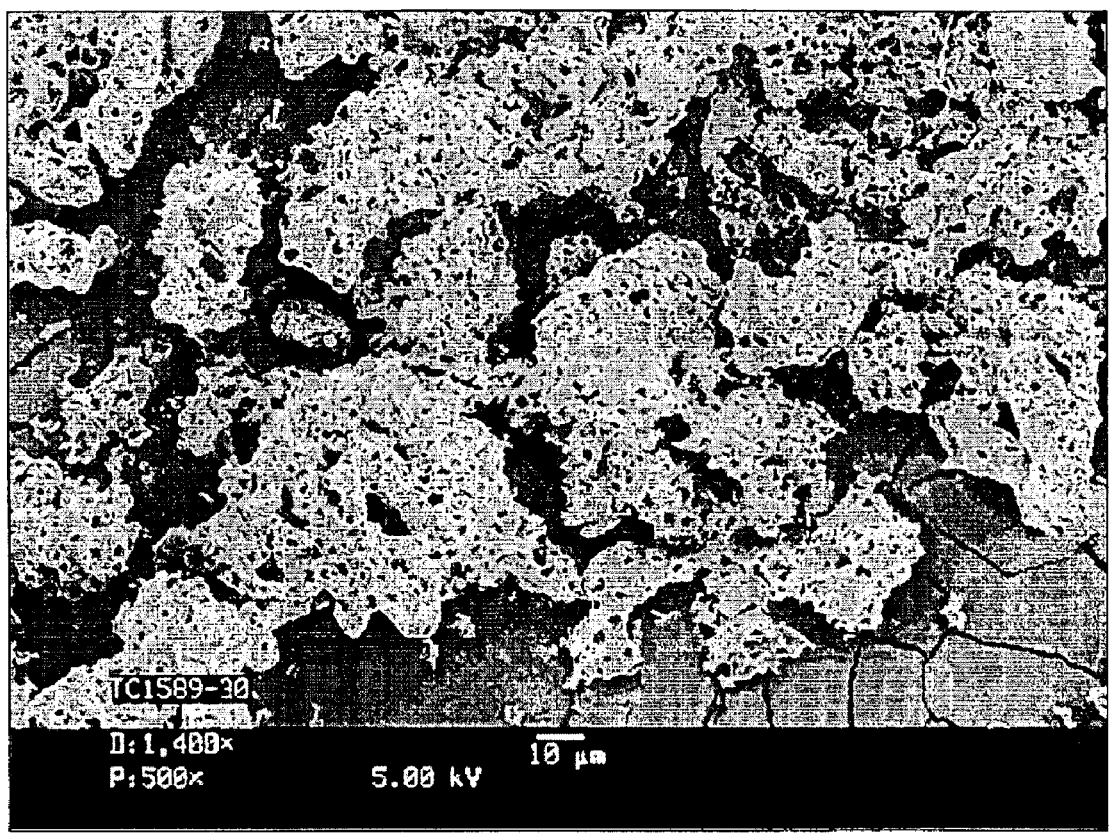
FIG. 7 is an SEM micrograph of Trehalose particles produced in EXAMPLE 4(g)

Analysis of the Lysozyme/Trehalose particles was performed using a Scanning Electron Microscope (SEM) to determine size and morphology. Laser diffraction instrument was used to determine particle size distribution. The dry product consisted of fine trehalose and lysozyme particles having a mean volume particle diameter below between 2 and 20 µm. The size increased with increasing trehalose concentration. Particles were porous with pores size varied between about 0.1 and 2 µm. Trehalose particles obtained in 4(g) are shown in FIG. 7.

TABLE 1

Concentrations of Lysozyme/Trehalose SOLUTIONS 4(a)–4(h).

| EXAMPLE | Trehalose (%) | Lysozyme (%) | Solution flow (ml/min) | $CO_2$ flow (ml/min) | Temp (° C.) |
|---|---|---|---|---|---|
| 4(a) | 2 | 2 | 5 | 100 | 38 |
| 4(b) | 2 | 2 | 10 | 100 | 38 |
| 4(c) | 2 | 2 | 10 | 100 | 60 |
| 4(d) | 10 | 2 | 10 | 100 | 38 |
| 4(e) | 10 | 2 | 2 | 100 | 38 |
| 4(f) | 20 | 2 | 10 | 100 | 38 |
| 4(g) | 40 | 0 | 10 | 100 | 38 |
| 4(h) | 0 | 2 | 10 | 100 | 38 |

Example 5

Preparation of Lysozyme/Trehalose Solution.

In an apparatus as shown in FIG. 1, lysozyme, with varying trehalose concentrations, was dissolved in purified water to form SOLUTIONS 5(a)–5(c). The concentrations are listed in TABLE 2.

TABLE 2

Concentrations of SOLUTIONS 5(a)–5(c).

| Example | Lysozyme (%) | Trehalose (%) |
|---|---|---|
| 5(a) | 2 | 0 |
| 5(b) | 2 | 2 |
| 5(c) | 2 | 5 |

Expansion and Freeze-drying of Lysozyme/Trehalose Particles.

SOLUTIONS 5(a)–5(c) were sequentially metered into the system at a $CO_2$ flow rate of 45 g/min and a solution flow rate of 4.5 ml/min. The SOLUTIONS 5(a)–5(c) were both heated to 38° C. (311 K) and were allowed to equilibrate in a solution tank with $CO_2$ at 27.5 MPa. Both the SOLUTIONS 5(a)–5(c) and the $CO_2$ were passed through a static mixing element before being expanded across a 150 µm capillary nozzle, similar to the nozzle shown in FIG. 4a, into the expansion chamber (2 L stainless steel vessel).

The expansion chamber was at atmospheric pressure, and the temperature of this chamber was maintained at below about 0° C. Frozen particles of solution and frozen particles of solvent were collected along with dry ice particles in the expansion chamber after spraying. The freeze-dry system was engaged and operated on the contents of the expansion chamber for about 12 hours.

Analysis of Lysozyme/Trehalose Particles

Figure 8:
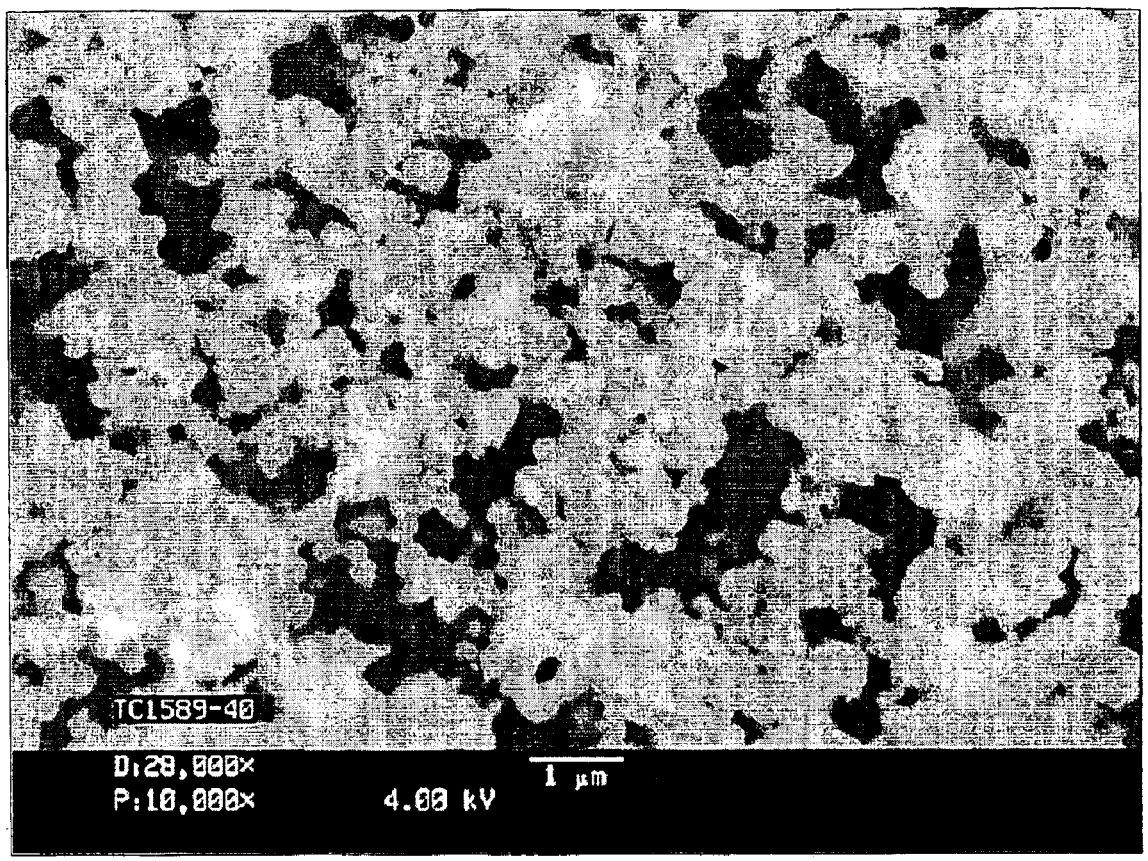
FIG. 8 is an SEM micrograph of Lysozyme particles produced in EXAMPLE 5(a)

Analysis of the Lysozyme/Trehalose particles was performed using a Scanning Electron Microscope (SEM) to determine size and morphology. Laser diffraction instrument was used to determine particle size distribution. FIG. 8 is an SEM micrograph of Lysozyme particles produced in EXAMPLE 5(a) in the size range between 0.1 and 0.5 µm. The composite Trehalose/Lysozyme particles had a mean particle diameter below 10 µm.

Example 6

Preparation of Lysozyme/Trehalose Solution.

In an apparatus as shown in FIG. 1, 2% lysozyme and 5% trehalose were dissolved in purified water to form SOLUTION 6(a).

Expansion and Freeze-drying of Lysozyme/Trehalose Particles.

SOLUTION 6(a) was metered into the system at a solution flow rate of 10 ml/min, and carbon dioxide was metered into the system at a $CO_2$ flow rate of 100 g/min. The flows of $CO_2$ and SOLUTION 6(a) were heated to 38° C. (311 K), and were allowed to equilibrate in a solution tank at 27.5 MPa. Both SOLUTION 6(a) and the $CO_2$ were passed through a static mixing element in a mixing chamber before being expanded across a 250 μm diameter capillary nozzle into an expansion chamber.

The expansion chamber had an internal diameter of 15.24 cm (6 inches) and a volume of approximately 20 liters. The expansion chamber was maintained at atmospheric pressure, and the temperature in the expansion chamber was maintained at below 0° Celsius. The temperature gradient was provided along the expansion vessel to avoid dry ice formation. Frozen particles of solution and frozen particles of solvent were collected in the expansion chamber after spraying. The freeze-dry system was engaged and operated on the contents of the expansion chamber for about 12 hours.

Analysis of Lysozyme/Trehalose Particles

Figure 9:
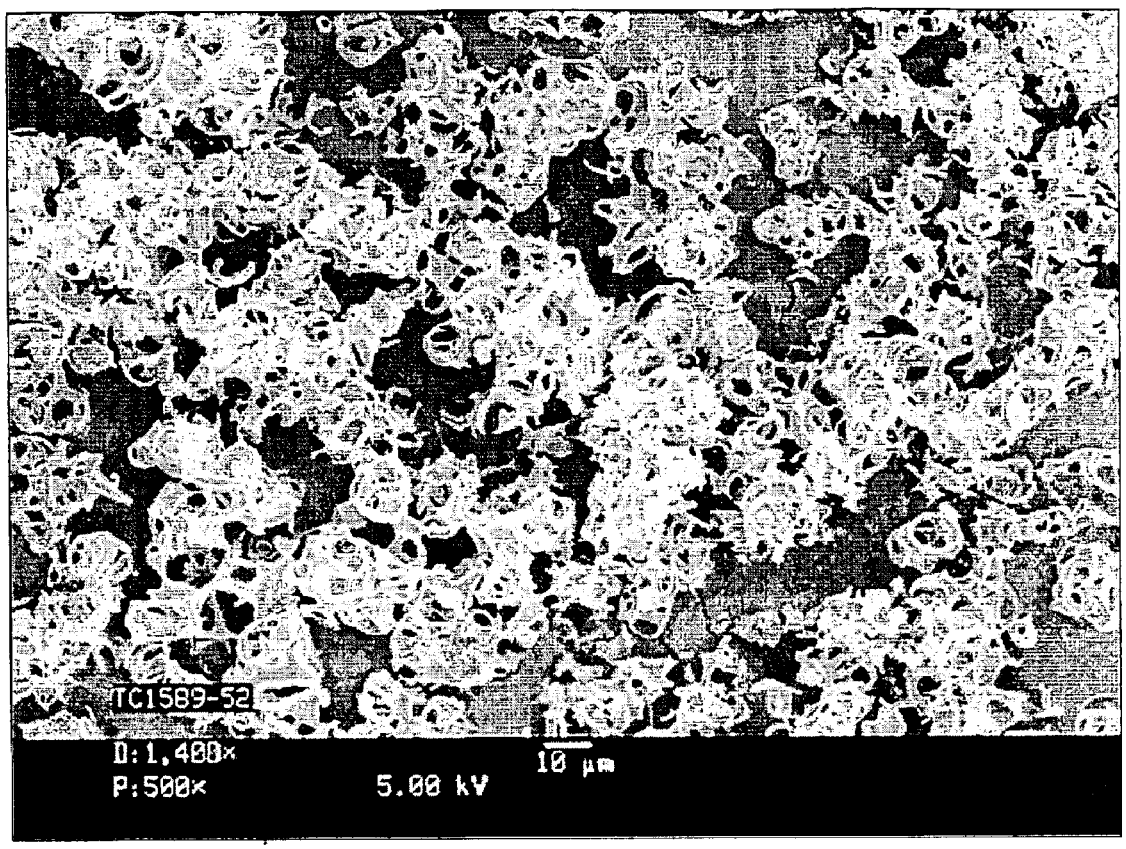
FIG. 9 is an SEM micrograph of Lysozyme/Trehalose particles produced in EXAMPLE 6.
Figure 10:
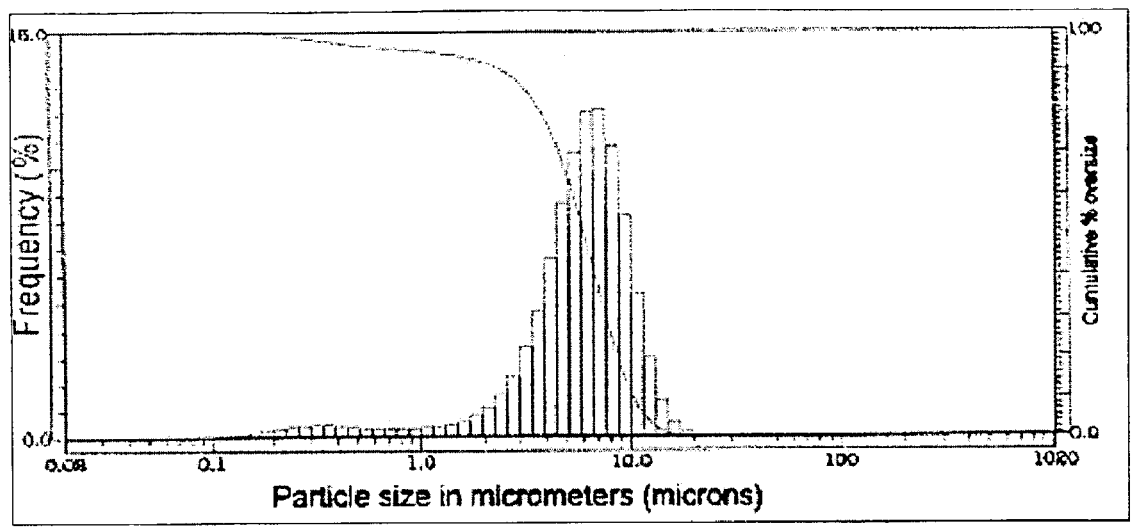
FIG. 10 is a particle size distribution of Lysozyme/Trehalose particles produced in EXAMPLE 6.

Analysis of the particles was performed using a Scanning Electron Microscope (SEM) to determine size and morphology and laser diffraction instrument was used to determine particle size distribution. FIG. 9 is an SEM micrograph of Lysozyme/Trehalose particles produced. FIG. 10 is a graph of Lysozyme/Trehalose particle size versus frequency of the particles produced. The dry product consisted of hollow composite trehalose/lysozyme particles with volume mean diameter about 6 μm. FIG. 9 shows the high surface area and hollow nature of the particles produced according to the present invention. The large pores form correspondingly large capillaries. The large capillaries in turn allow for a reduced time requirement for lyophilization.

Example 7

Preparation of Trypsinogen/Trehalose Solution.

In an apparatus as shown in FIG. 1, SOLUTIONS 7(a)–7(e) of trypsinogen with varying trehalose concentrations in purified water were prepared. These compositions of SOLUTIONS 7(a)–7(e) are listed in TABLE 3.

Expansion and Freeze-drying of Trypsinogen/Trehalose Particles.

SOLUTIONS 7(a)–7(e) were independently and sequentially metered into the system at a $CO_2$ flow rate of 100 g/min and a solution flow rate of 10 ml/min. The $CO_2$ flow was heated to 32° C. (305 K), the solution was held at room temperature (22° C. (295 K)). The solution and the $CO_2$ were allowed to equilibrate in a solution tank at 27.5 MPa, and then both the solution and the $CO_2$ were passed through a static mixing element before being expanded across a 250 μm capillary nozzle into the expansion chamber.

The expansion chamber has an internal diameter of 6" (15.24 cm) with a volume of approximately 20 liters. It was maintained at atmospheric pressure, and the temperature of this chamber was maintained at below 0° C. Frozen particles of solution and frozen particles of solvent were collected along with dry ice particles in the expansion chamber after spraying. The freeze-dry system was engaged and operated on the contents of the expansion chamber for about 12 hours.

Analysis of Trypsinogen/Trehalose Particles

Analysis of the particles was performed using a Scanning Electron Microscope (SEM) to determine size and morphology and laser diffraction instrument was used to determine particle size distribution. The dry product included fine trehalose/trypsinogen particles with a volume mean particle diameter as shown in TABLE 3. Bioactivity assay was carried out as described in the reference (C. Sonner et al, Journal of Pharmaceutical Sciences, Vol. 91, No. 10, October 2002, pages 2122–2139). The results showed that processing with sugars according to this invention preserved the activity of proteins to be above 80% at sugar concentrations above 50% by mass.

TABLE 3

Particle size and relative percentage of EXAMPLES 7(a)–7(e).

| EXAMPLE | Trypsinogen (%) | Trehalose (%) | Particle size (μm) |
|---------|-----------------|---------------|--------------------|
| 7(a)    | 1               | 0             | 0.79               |
| 7(b)    | 1               | 1             | 5.57               |
| 7(c)    | 1               | 5             | 7.7                |
| 7(d)    | 1               | 10            | 9.88               |
| 7(e)    | 1               | 20            | 14.58              |

Example 8

Preparation of Lysozyme/Trehalose Solution.

Similar to EXAMPLE 7, SOLUTION 8(a) of 2% lysozyme with 10% trehalose in purified water was prepared. In addition, a nozzle was constructed and aligned axially or perpendicular and just below the $CO_2$/solution nozzle as shown in FIGS. 4(b) and 4(d), respectively. Nitrogen was delivered to this nozzle from a high-pressure bottle regulated to a pressure of 2000 psig. The nozzles were about 10 mm apart, and the flows directly impinged axially or perpendicularly. This configuration caused increased dispersion and mixing in a plume region and a different temperature in the expansion zone.

Expansion and Freeze-drying of Lysozyme/Trehalose Particles.

SOLUTION 8(a) was metered into the system at a $CO_2$ flow rate of 45 g/min and a solution flow rate of 4.5 ml/min. The $CO_2$ and SOLUTION 8(a) flows were heated to 38° C. (311 K), and were allowed to equilibrate in a solution tank at 27.5 MPa, and then both SOLUTION 8(a) and the $CO_2$ were passed through a static mixing element before being expanded across a 250 μm capillary nozzle into the expansion chamber.

The expansion chamber has an internal diameter of 6" (15.24 cm) with a volume of approximately 20 liters. It was maintained at atmospheric pressure, and the temperature of this chamber was maintained at below 0° C. Frozen particles of solution and frozen particles of solvent were collected along with dry ice particles in the expansion chamber after spraying. The freeze-dry system was engaged and operated on the contents of the expansion chamber for about 12 hours.

Analysis of the Lysozyme/Trehalose Particles

Figure 11:
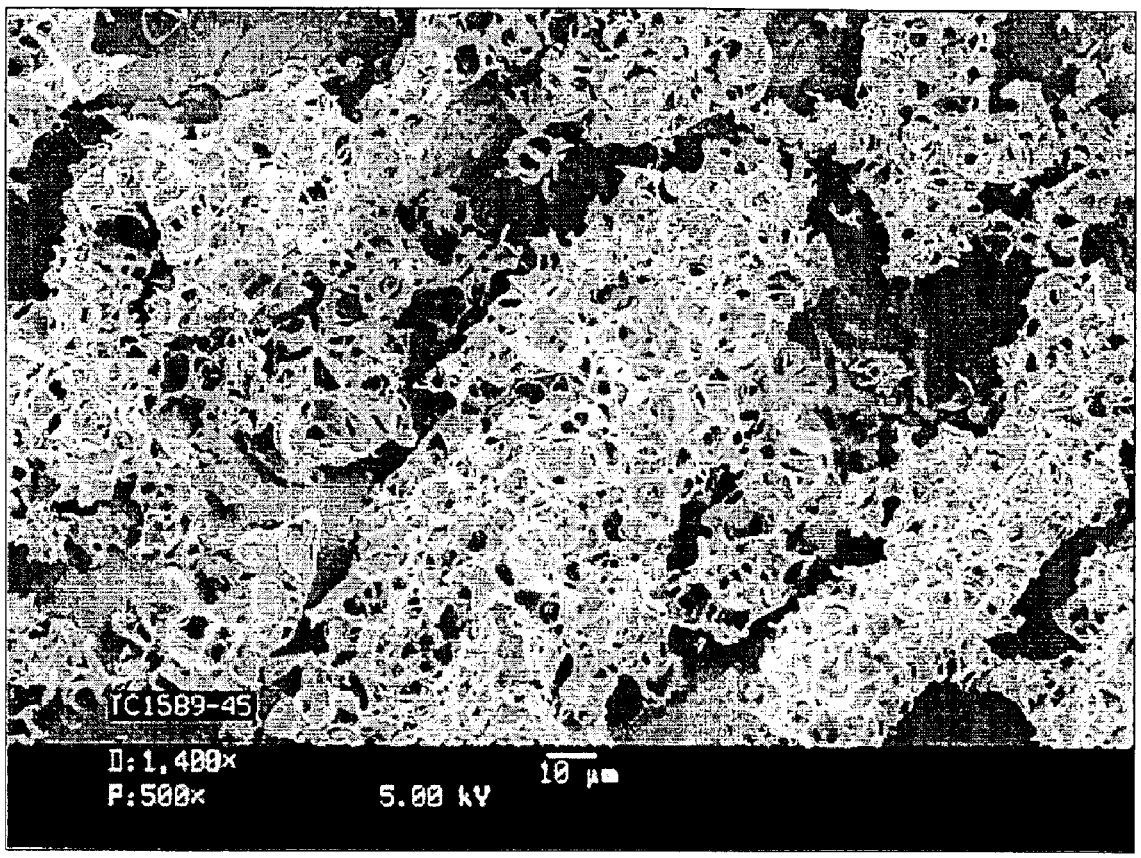
FIG. 11 is an SEM micrograph of Lysozyme/Trehalose particles produced in EXAMPLE 8.

Analysis of the Lysozyme/Trehalose particles was performed using a Scanning Electron Microscope (SEM) to determine size and morphology. The dry product consisted of fine trehalose and lysozyme composite particles having a mean particle diameter below 20 μm. The SEM micrograph of the particles produced in EXAMPLE 8(a) is shown in FIG. 11

Example 9

Preparation of Lysozyme/Trehalose Solution.

In an apparatus as shown in FIG. 1, 2% lysozyme and 10% trehalose were dissolved in purified water to prepare SOLUTION 9(a).

Expansion and Freeze-drying of Lysozyme/Trehalose Particles.

SOLUTION 9(a) was metered into the system with a $CO_2$ flow rate of 100 g/min and a solution flow rate of 10 ml/min. The $CO_2$ and SOLUTION 9(a) flows were heated to 38° C. (311 K), and were allowed to equilibrate in a solution tank at 27.5 MPa, and then both the solution and the $CO_2$ were passed through a static mixing element before being expanded across a 150 µm capillary nozzle into the expansion chamber.

The expansion chamber has an internal diameter of 6" (15.24 cm) with a volume of approximately 20 liters. It was maintained at atmospheric pressure, and the temperature of this chamber was maintained at below 0° C. Frozen particles of solution and frozen particles of solvent were collected along with dry ice particles in the expansion chamber after spraying.

Figure 12:
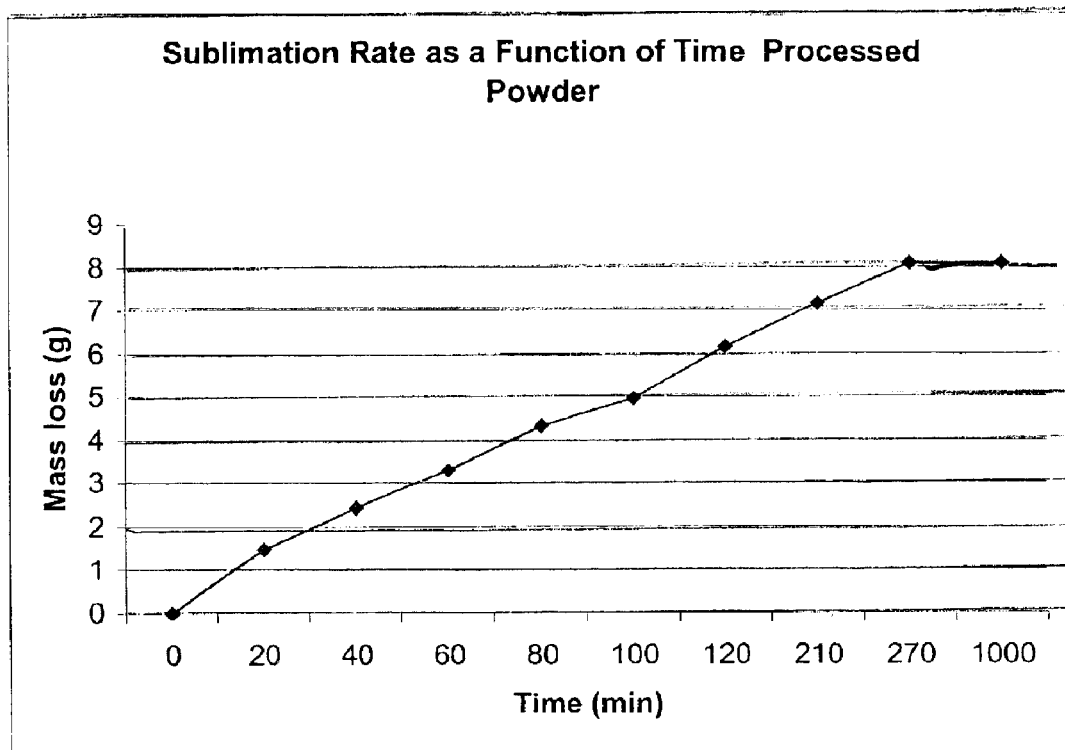
FIG. 12 is a diagram showing dependence of sample weight versus drying time during a lyophilization process according to EXAMPLE 9.

The frozen particles of solvent and solution were then collected in a 600 ml lyophilization flask of known mass. The mass of the frozen sample was then determined, and the sample was then engaged with the freeze-dry system. The sample was weighed at specified intervals of time, and the change in mass was recorded. Temperature of the sample was also recorded at each interval. These results are shown in FIG. 12.

SOLUTION 9(b) was prepared in a manner similar to SOLUTION 9(a), and was weighed out to the same mass as SOLUTION 9(a). To form a comparitive example, SOLUTION 9(b) was placed into a similar 600 ml tared lyophilization flask, and held at -25° C. for several hours. It was also engaged with the freeze-dry system, and was weighed at similar intervals as the processed sample. Change in mass as well as temperature of the material was also recorded.

Analysis of Lysozyme/Trehalose Particles

Analysis of the Lysozyme/Trehalose particles was performed using a Scanning Electron Microscope (SEM) to determine size and morphology. The dry product obtained using this invention consisted of fine trehalose/lysozyme composite particles having a mean particle diameter below 10 µm with a powder bulk density below 0.1 $g/cm^3$. The drying was completed after 12 hours. The particles were formed as flakes with a typical size above 100 µm and powder density above 0.2 $g/cm^3$. SEM micrographs of comparitive examples obtained by conventional solution freezing techniques (as in a standard lyophilization method) collapsed or melted during the freeze-drying step. The drying rate for this product was also shown to be longer than for the product obtain according to the present invention.

The processes and embodiments described herein are examples of structures, systems and methods having elements corresponding to the elements of the invention recited in the claims. This written description may enable those skilled in the art to make and use embodiments having alternative elements that likewise correspond to the elements of the invention recited in the claims. The intended scope of the invention thus includes other structures, systems and methods that do not differ from the literal language of the claims, and further includes other structures, systems and methods with insubstantial differences from the literal language of the claims.

What is claimed is:

1. An apparatus for producing particles comprising:
    a solution source for supplying a solution comprising a solvent and a solute;
    a supercritical fluid source for supplying a supercritical fluid;
    a mixer in fluid communication with the solution source and the supercritical fluid source for mixing the solution and the supercritical fluid together to form a mixture, and for maintaining the mixture at a first pressure sufficiently high so as to maintain the supercritical fluid in a supercritical state;
    an expansion assembly comprising an expansion vessel having an inner surface defining an expansion chamber that is in fluid communication with the mixer for spraying the mixture across a pressure drop to form mixture droplets, the mixture droplets comprising the solute and frozen solvent;
    a thermostat that is operable to control a temperature in the expansion chamber to be below the solution freezing temperature; and
    a freeze-dry apparatus that is in communication with the expansion assembly for sublimating the frozen solvent, and thereby removing the frozen solvent from the solute, whereby solute particles are produced that are generally free of the solvent.

2. The apparatus as defined in claim 1 wherein the expansion assembly receives the mixture from the mixer at the first pressure, and sprays the mixture at a second, lower pressure such that a portion of the fluid expands in response to a change from the first pressure to the second lower pressure, the expansion of the fluid portion reducing a temperature of the mixture so as to be below a freezing point of the solution.

3. The apparatus as defined in claim 1 wherein the solvent is selected from the group consisting of water, alcohol, toluene, ethyl acetate, methyl chloride, methylene chloride, dimethyl sulfoxide (DMSO), dimethyl formamide (DMF), or other organic or inorganic solvents.

4. The apparatus as defined in claim 1 wherein the solute is selected from the group consisting of polymer, filler, disintegrant, binder, solubilizer, excipient, surfactant, and combinations thereof.

5. The apparatus as defined in claim 4 wherein the solute is a polymer selected from the group consisting of polysaccharide, polyester, polyether, polyanhydride, polyglycolide (PLGA), polylactic acid (PLA), polycaprolactone (PCL), polyethylene glycol (PEG), or polypeptide.

6. The apparatus as defined in claim 1 wherein the solute is selected from the group consisting of a biologically active material, drug, pharmaceutical, pharmaceutical excipient, therapeutic agent, medicinal agent, sugar, pigment, toxin, insecticide, viral material, diagnostic aid, agricultural chemical, nutritional material, protein, alkyloid, alkaloid, peptide, animal extract, plant extract, dye, explosive, paint, cosmetic, antigen, enzyme, catalyst, nucleic acid, zeolite, polymer precursor, and combinations thereof.

7. The apparatus as defined in claim 6 wherein the solute further comprises a polymer, filler, disintegrant, binder, solubilizer, stabilizer, buffer or combinations thereof.

8. The apparatus as defined in claim 6 wherein the solution further comprises a surfactant or a processing aid.

9. The apparatus as defined in claim 1 wherein the supercritical fluid comprises carbon dioxide, nitrous oxide, propane, or ethane.

10. The apparatus as defined in claim 1 further comprising a controller communicating with the solution source, the supercritical fluid source, the mixer and the freeze-dry apparatus, the controller being operable to:

control flow rates of solution and supercritical fluid from the respective solution source and supercritical fluid source to the mixer, control the mixing rate of the mixer to mix the solution and supercritical fluid to form the mixture, control the mixer to supply the mixture to the expansion assembly at a predetermined flow rate, and control the freeze-dry apparatus to sublime the solid solvent particles at a predetermined rate of solvent extraction.

11. The apparatus as defined in claim 1 wherein the mixer is further operable to mix the solution and the supercritical fluid such that the solution is saturated with the supercritical fluid or is dispersed within the supercritical fluid.

12. The apparatus as defined in claim 1 wherein the frozen solvent constitutes the same phase as the solute particles.

13. An apparatus for producing particles comprising:

a solution source supplying a solution comprising a solvent and a solute;

a fluid source supplying a compressed fluid, wherein the compressed fluid comprises a first fluid component and a second fluid component that have freezing points at different temperatures relative to each other, and the first fluid component has a higher freezing point relative to the second fluid component, and the first fluid component operates as a blowing or expanding agent and the second fluid component operates as a freezing agent;

a mixer in fluid communication with the sources for mixing the solution and the compressed fluid together to form a mixture, and for maintaining the mixture at a first pressure sufficiently high so as to maintain the compressed fluid in a compressed state;

an expansion assembly in fluid communication with the mixer for spraying the mixture across a pressure drop to form mixture droplets, the expansion assembly comprising a nozzle configured so that the solution and fluid are sprayed therethrough, the nozzle being further configured to have a contra-current, co-axial, single or multiple opening configuration, the mixture droplets comprising the solute and frozen solvent; and a freeze-dry apparatus that is in communication with the expansion assembly for subliming the frozen solvent, and thereby removing the frozen solvent from the solute, whereby solute particles are produced that are generally free of the solvent.

14. The apparatus as defined in claim 13 wherein the blowing or expanding agent and the freezing agent have different chemical structures from each other, and optionally have the same or a different temperature immediately subsequent to mixing with the solution.

* * * * *